(12) United States Patent
Singh

(10) Patent No.: US 6,869,429 B2
(45) Date of Patent: Mar. 22, 2005

(54) APPARATUS FOR EXTERIOR ARTERIAL ABLATION

(76) Inventor: Ajoy Inder Singh, #6, 2nd Floor, Shiv-Smurti, 32-33 Union Park, Pali Hill, Mumbai (IN), 400 052

( * ) Notice: Subject to any disclaimer, the term of this patent is extended or adjusted under 35 U.S.C. 154(b) by 0 days.

(21) Appl. No.: 10/713,277

(22) Filed: Nov. 17, 2003

(65) Prior Publication Data

US 2004/0111085 A1 Jun. 10, 2004

Related U.S. Application Data

(62) Division of application No. 09/619,625, filed on Jul. 19, 2000, now Pat. No. 6,669,686.

(30) Foreign Application Priority Data

Jul. 20, 1999 (GB) .............................. 9917026

(51) Int. Cl.[7] .............................. A61B 18/18
(52) U.S. Cl. .............................. 606/11; 606/2; 606/7; 606/10; 606/14; 606/159; 606/167
(58) Field of Search ....................... 606/1–3, 7, 10–17, 606/159, 167–173

(56) References Cited

U.S. PATENT DOCUMENTS

| | | |
|---|---|---|
| 4,785,806 A | 11/1988 | Deckelbaum |
| 5,109,859 A | 5/1992 | Jenkins |
| 5,127,902 A * | 7/1992 | Fischell .................. 604/22 |
| 5,254,112 A * | 10/1993 | Sinofsky et al. ............ 606/10 |
| 5,346,488 A | 9/1994 | Prince et al. |
| 5,720,894 A | 2/1998 | Neev et al. |
| 5,755,682 A * | 5/1998 | Knudson et al. ............ 604/8 |
| 6,196,230 B1 * | 3/2001 | Hall et al. ................. 606/194 |

FOREIGN PATENT DOCUMENTS

| | | |
|---|---|---|
| EP | 0329492 | 8/1989 |
| WO | 9907904 | 7/1990 |

* cited by examiner

Primary Examiner—Glenn K. Dawson
Assistant Examiner—Michael G. Mendoza
(74) Attorney, Agent, or Firm—Dowell & Dowell, P.C.

(57) ABSTRACT

A method and apparatus for reducing the thickness of arterial walls is disclosed. Ablation of the exterior layer of the arterial walls is performed using mechanical or laser ablation techniques. Surveying is preferably carried out during the procedure to ensure optimal ablation. The ablation reduces the effective thickness of the arterial walls and increases flexibility so that the walls distend under normal blood pressure, thereby improving blood flow. Advantageously, the procedure is carried out without invasion of the blood vessel lumen and without damage to the inner layer of the artery wall.

13 Claims, 5 Drawing Sheets

APPARATUS FOR EXTERIOR ARTERIAL ABLATION

CROSS REFERENCE TO RELATED APPLICATIONS

This application is a divisional application and claims benefits under 35 U.S.C. 120 with respect to U.S. application Ser. No. 09/619,625 filed Jul. 19, 2000 now U.S. Pat. No. 6,669,686 in the name of the same inventor.

BACKGROUND OF THE INVENTION

1. Field of the Invention

This invention relates to arterial ablation. By way of non-limiting example the invention may be usable to relieve arterial blockage due to atherosclerosis, for example.

2. Description of the Related Art

Arteries affected by diseases such as atherosclerosis may have increased arterial wall thickness due to deposits of cholesterol and cellular proliferation. This leads to increased arterial wall stiffness and reduced internal diameter, and consequently reduced blood flow though the artery.

Hitherto medical intervention to arterial wall thickening has been endoluminal, that is, from the inside of the vessel, such as catheter based balloon angioplasty, laser angioplasty and atherectomy. Such procedures are relatively complex because the blood supply through the artery must be diverted. In addition, endoluminal intervention necessarily involves injury to the internal layer of the artery wall, the tunica intima. The damaged tunica intima heals by intimal hyperplasia and fibrosis. In a significant number of cases, estimated at 25%, the treated vessel is re-blocked within 6 months.

There is a need for a method and apparatus for increasing the flexibility of an arterial wall thickened by disease, in order to increase blood flow through the artery, which is more effective than known techniques and is less likely to result in re-blockage of the artery.

SUMMARY OF THE INVENTION

This invention seeks to allow treatment of arterial wall thickening with less or no damage in the tunica intima, thereby avoiding re-blockage due to hyperplasia of the tunica intima during the healing thereof.

It has been unexpectedly found that ablation of the external layer of the artery wall, the tunica adventitia, optionally in conjunction with part of the middle layer of the arterial wall, the tunica media, is effective for reducing or eliminating arterial wall thickening.

According to an aspect of the invention there is provided a method for reducing the thickness of an arterial wall by ablation of the exterior of the artery wall.

By ablating the exterior layer of the arterial wall, the tunica intima and inner layers of the tunica media are protected from damage. Re-blockage cannot thereafter be caused by hyperplasia during healing of the tunica intima. The flexibility of the artery is improved due to the reduced effective wall thickness after ablation thus relieving stenosis and improving blood flow through the artery.

In addition, the procedure may be carried out without diverting the blood flow through the artery.

According to another aspect of the invention there is provided apparatus for relieving arterial blockage comprising:

i) apparatus for surveying the thickness of an arterial wall, and ii) apparatus for ablating the exterior of the arterial wall to increase the flexibility of the arterial wall.

Further preferred features and advantages of the present invention will become apparent from the following description and accompanying claims.

BRIEF DESCRIPTION OF THE DRAWINGS

Embodiments of the invention will be described by way of non-limiting example by reference to the accompanying drawings, of which.

DETAILED DESCRIPTION OF THE PREFERRED EMBODIMENTS

As an initial step, digital simulations of the response of a flexible tube to alternations in its wall thickness while maintaining the internal fluid pressure and wall flexibility were carried out. The results were checked against Laplace's law giving a good correlation. Subsequently excised porcine carotid arteries (both healthy and diseased) were studied. The arterial wall was sequentially ablated mechanically and its response to internal hydrostatic pressure determined. The results were sufficiently promising for further work to be conducted.

Figure 1:
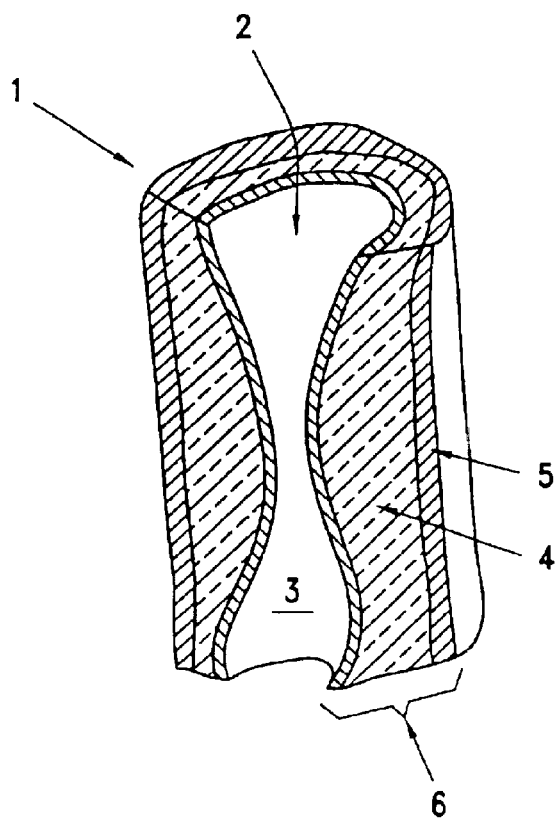
FIG. 1 is partially sectioned perspective schematic view of an atherosclerosed artery having a thickened wall.

Referring to FIG. 1, artery 1 has lumen 2 defined by tunica intima 3. Tunica media 4 lies intermediate tunica intima 3 and tunica adventitia 5. Atherosclerosis is characterised by enlargement of the artery wall 6 comprising tunica intima 3 tunica media 4 and tunica adventitia 5. Enlargement of artery wall 6 results in restriction of lumen 2. Principally restriction is due to atherosclerotic plaque and/or enlarged tunica media. It will be appreciated that other causes of thickened arterial walls are known. Whilst the following description concerns the ablation of an atherosclerosed artery, it will be appreciated that the present invention can be used to treat arterial walls thickened due to other causes such as cellular hyperplasia.

In accordance with the invention, the first step comprises surveying the atherosclerosed artery. Examples of suitable techniques include ultrasound imaging, magnetic resonance imaging, electromagnetic radiation based tomographic imaging and photonic imaging. The list is by no means exhaustive. Those skilled in the art will readily appreciate other techniques can be used. The surveying step should allow precise mapping of the artery. Desirably the mapping will provide a 3D image of the artery. Desirably the surveying step is performed in real time to allow monitoring and feedback for the subsequent steps. Preferably computed optical tomographic imaging in reflective mode using a pulsed infra-red laser is used.

Figure 2:
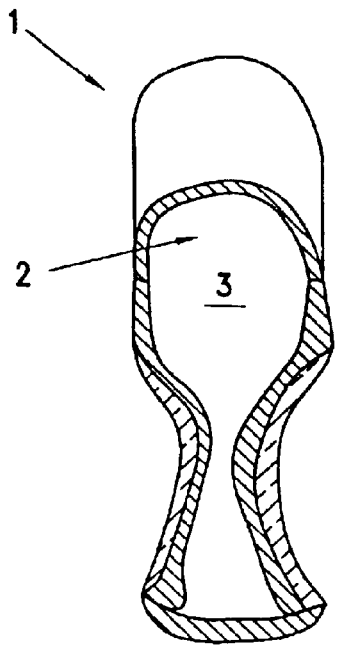
FIG. 2 is a partially sectioned perspective schematic view of the artery of FIG. 1 following ablation in accordance with the invention.
Figure 3:
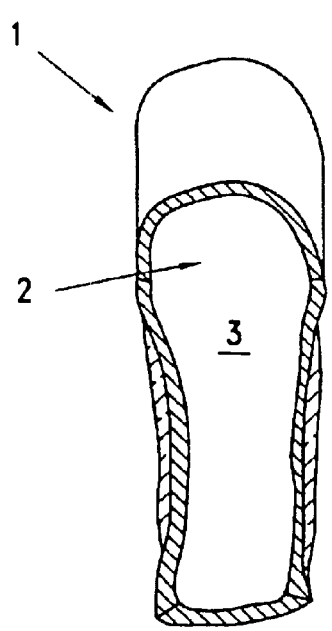
FIG. 3 is a partially sectioned perspective schematic view of the artery of FIG. 2 following expansion due to pressure within the arterial lumen.

The second step comprises ablating the exterior of the artery so that it becomes more flexible. FIG. 2 shows the artery of FIG. 1 with the tunica adventitia 5 and external layers of the tunica media 4 ablated in the affected area. Once subjected to internal blood pressure the lumen dilates relieving the blockage as shown in FIG. 3.

Figure 4:
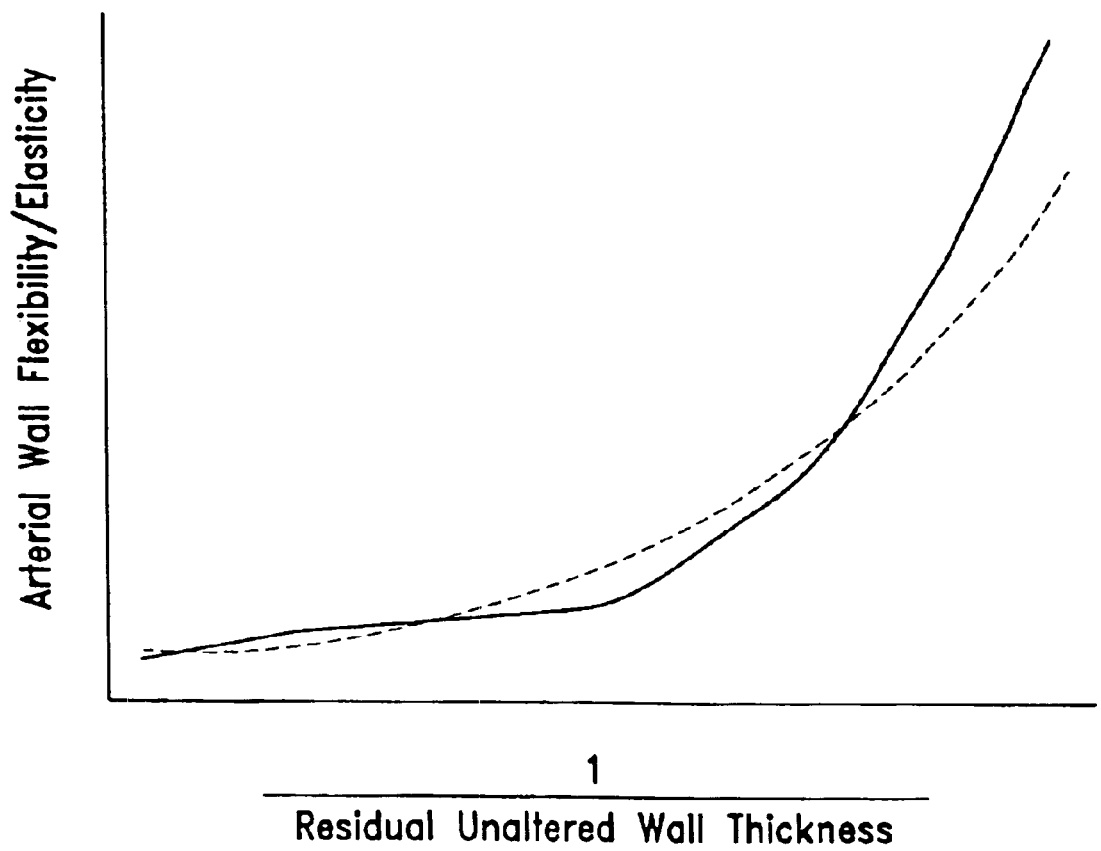
FIG. 4 is a graph showing the relationship between arterial wall flexibility and the residual arterial wall thickness.

It has been found that as the residual arterial wall thickness is reduced the arterial wall elasticity and flexibility increases. An example of the experimentally determined relationship is illustrated in FIG. 4.

Examples of ablation techniques include the use of high energy lasers. Examples of this include femto-second pulsed laser. Preferred lasers provide pulses of 20 to 100 fs duration, 3 to 5 $J/cm^2$ fluence and 10 to 100 $\mu$m spot diameter. Preferably the photons have sufficient energy to break molecular bonds within the tissue. This allows ablation without serious thermal injury to adjacent cells. Ablation can be rapid: one micron per pulse at one thousand pulses per second can be achieved.

It is recommended that fluence is less than 30 $J/cm^2$. In general, with decreasing pulse width, the fluence also declines. Ablation would typically begin at a fluence of about 3 $J/cm^2$ with a pulse width of less than 300 fs and continues with higher energies. Fluence of up to 25 $J/cm^2$ has been employed without any ill effects. However, for femto-second pulsed laser ablation, the ablation rate is independent of fluence for fluences above 3 $J/cm^2$, and so higher fluence provides no particular advantage.

In some embodiments ablation is controlled to ablate the artery wall to leave a generally uniform residual arterial wall thickness. By surveying during ablation, the ablation can be controlled to produce the desired, optimal wall thickness as described below. Insufficient ablation will not produce enough enlargement of the lumen. Excessive ablation results in aneurysm and ultimate rupture of the arterial wall. Those skilled in the art will have little difficulty in assessing suitable amounts of ablation. The ultimate wall thickness will vary according to the blood vessel but for carotid arteries may be in the range 600 to 1100 $\mu$m such as about 800 $\mu$m.

The invention is useful for treating a range of arteries. Arterial diameter varies. Carotid arteries can have an internal diameter up to 9 mm whereas coronary arteries may have an internal diameter as small as 1 mm. The normal wall thickness varies but there is a general constant relationship between internal diameter, wall thickness and flexibility. Accordingly the skilled in the art will have little difficulty in determining the appropriate degree of ablation.

The technique is particularly useful for serious atherosclerosis which may be life-threatening in the short time. Where the atherosclerosis is not so pronounced complete ablation of the plaque may not be necessary. For example in one embodiment of the invention a plurality of small holes are 'drilled' in the tunica adventitia as far as the atherosclerotic plaque with, for example, ultra-short pulsed laser radiation. The plaque can then be melted for example with a pulsed IR laser. The plaque leaches out and is destroyed by macrophages.

In a further embodiment of the invention a plurality of furrows are formed in the exterior of the arterial wall for example using an ultra-short pulsed laser. The preferred depth of the furrows varies from artery to artery. Blood pressure inside the artery distends it and relieves the blockage. Macrophages have access to the atheroma via the furrows and can, over time mobilise amorphous material from it. A relatively small number for example 2 to 6 preferably 3, 4 or 5 longitudinal furrows may be produced together with a large number of transverse furrows.

Atheroma ablation is conducted at the site of the blockage caused by the atherosclerotic plaque. The plaque is responsible for i) increased arterial wall thickness;
ii) reduced arterial wall flexibility; and
iii) loss of pulsation.

Before ablation the arterial wall is non-pulsatile due to its stiff, thickened structure. As ablation proceeds the residual wall thickness decreases and becomes more flexible. A point is then reached at which the wall is (minimally) pulsatile in response to the systolic and diastolic pressure in the artery. This indicates the return of adequate arterial wall flexibility. Usually no further ablation is required. If the ablation is performed whilst blood is flowing through the artery, the skilled person will be able to determine from the pulsatile movement of the artery wall that ablation is complete. Imaging apparatus, as described below, may be employed for monitoring the artery during ablation, and the imaging data used to determine the point in the procedure qt which ablation is complete. The ideal residual arterial wall thickness is generally 1.3 to 1.5 times the normal wall thickness of non-diseased artery but may vary, for example, in the presence of calcific disease and other arterial degenerations.

While described by reference to laser ablation those skilled in the art will appreciate that other means for ablating the tunica adventitia and media could be used, for example, mechanical ablation using a surgical blade.

Figure 5:
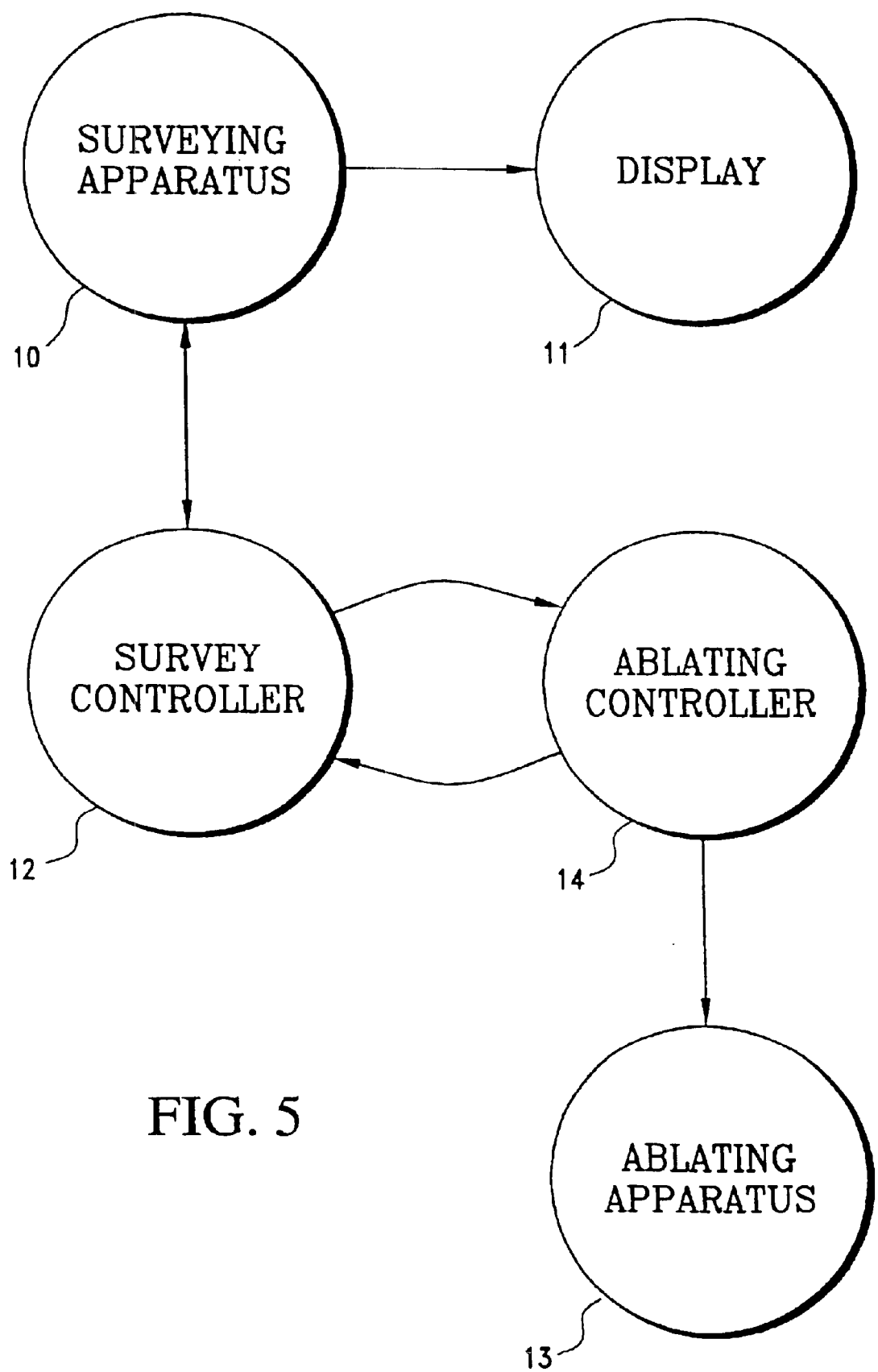
FIG. 5 is a block diagram of suitable apparatus in accordance with the invention.

FIG. 5 is a block diagram which illustrates the various functional parts of an apparatus for use in the invention. The apparatus comprises apparatus 10 for surveying the artery. In accordance with the preferred embodiments described below with reference to FIGS. 6 and 7, the surveying apparatus 10 is an imaging system using coherence optical tomography such as an Optical Computed Tomography (OCT) system. As is well known in the art, the scanning beam of such an imaging system is reflected by a mirror and scans the underlying tissue, including the artery. The reflected beam is analysed to produce a three-dimensional rendering of the artery. In accordance with the invention, the image data thereby produced is then used for accurate positioning and control of the ablation apparatus. Preferably the imaging system uses a low intensity infra red laser to produce the image of the underlying tissue. The associated software produces a distance map and three-dimensional model of the artery. The necessary positioning, movement and control of the ablation apparatus are computed using the image data for reducing the thickness of the artery at the site of the stenosis.

Referring again to FIG. 5, the apparatus preferably further includes a display 11 for displaying the results of survey (image) may be connected to the surveying apparatus 10 for viewing by the surgeon. Surveying apparatus 10 may be connected to survey controller 12. Ablating apparatus 13, such as the aforementioned femto-second pulsed laser, is provided and desirably connected to ablating controller 14. The ablating controller 14 is employed to precisely control the ablating apparatus to ensure the high degree of precision necessary for successful ablation. In preferred embodiments of the apparatus according to the invention, ablating controller 14 is connected to survey controller 12 such that a feed back loop is established. Thus, by feeding back data from the surveyor 10 to the ablator controller 14 as it moves the ablator automated reciprocal ablation can be achieved. In particular, reciprocal ablation is performed to leave behind a uniform unaltered residual arterial wall thickness. Excess tissue on the external surface of the artery is ablated so that the external topography reciprocally mimics the topography of the internal lining of the artery.

The ablating apparatus 10, under control of the ablating controller 14 makes incisions of controlled depth in the arterial wall, thereby reducing the effective arterial wall thickness and increasing flexibility. The artery wall may then distend under physiological blood pressure to improve blood flow through the artery.

The surveying apparatus 10 and controller 12 can identify the above-mentioned point in time during the ablation process where the arterial wall becomes minimally pulsatile and has adequate flexibility. In particular, reappearance of arterial wall pulsatality is detected by online monitoring by the surveying apparatus 10 e.g. an OCT system. An increase in luminal diameter of the artery is detected in response to changes in arterial pressure. When this point is reached, it signals to the ablating controller 14 to terminate the ablation process.

Figure 6:
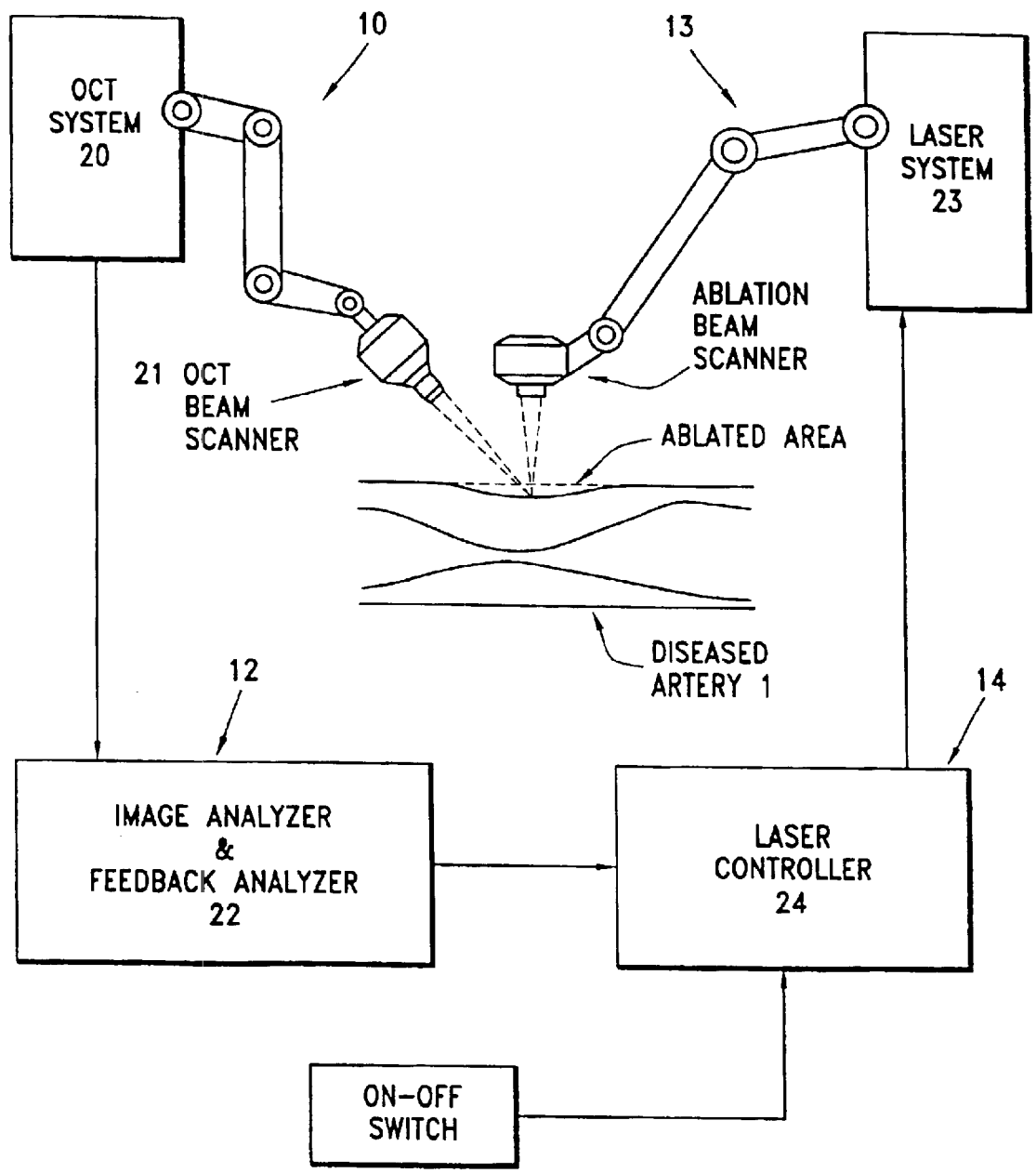
FIG. 6 is a schematic view of the apparatus of FIG. 5 in accordance with a first preferred embodiment of the invention.

FIG. 6 illustrates an apparatus of a first preferred embodiment of the invention in use, in which the ablating apparatus 13 is a laser system 23 comprising a femto-second pulsed laser. The surveying apparatus 10 comprises an OCT system 20, which includes an OCT beam scanner 21, which scans the diseased artery 1 and provides the scanned data to an image analyser and feedback analyser 22. The image analyser 22 produces a three-dimensional model of the artery 1 which is analysed by the feedback analyser 22 to determine the necessary additional ablation required. The data is then fed back to a laser controller 24 which controls the laser system 23 to perform further ablation.

An alternative method for determining when ablation is complete, which may be used alone or in addition to monitoring for the return of pulsatile movement, is to determine when adequate luminal diameter is achieved. In this method, the system estimates the arterial wall thickness underlying each point on the arterial wall surface. The desired depth of ablation for each spot is estimated using the formula:

$$z+(y-2x)/2,$$

where x=arterial wall thickness in normal subjects with healthy arteries; y=wall thickness of diseased artery; and z=desired depth of ablation. This process of imaging followed by ablation to the predetermined depth is repeated several times (the value of z is calculated afresh each time), until the OCT system indicates an adequate internal luminal diameter of the blood vessel under treatment. This method is especially useful for heavily calcified arteries that tend to pulsate rather poorly.

Figure 7:
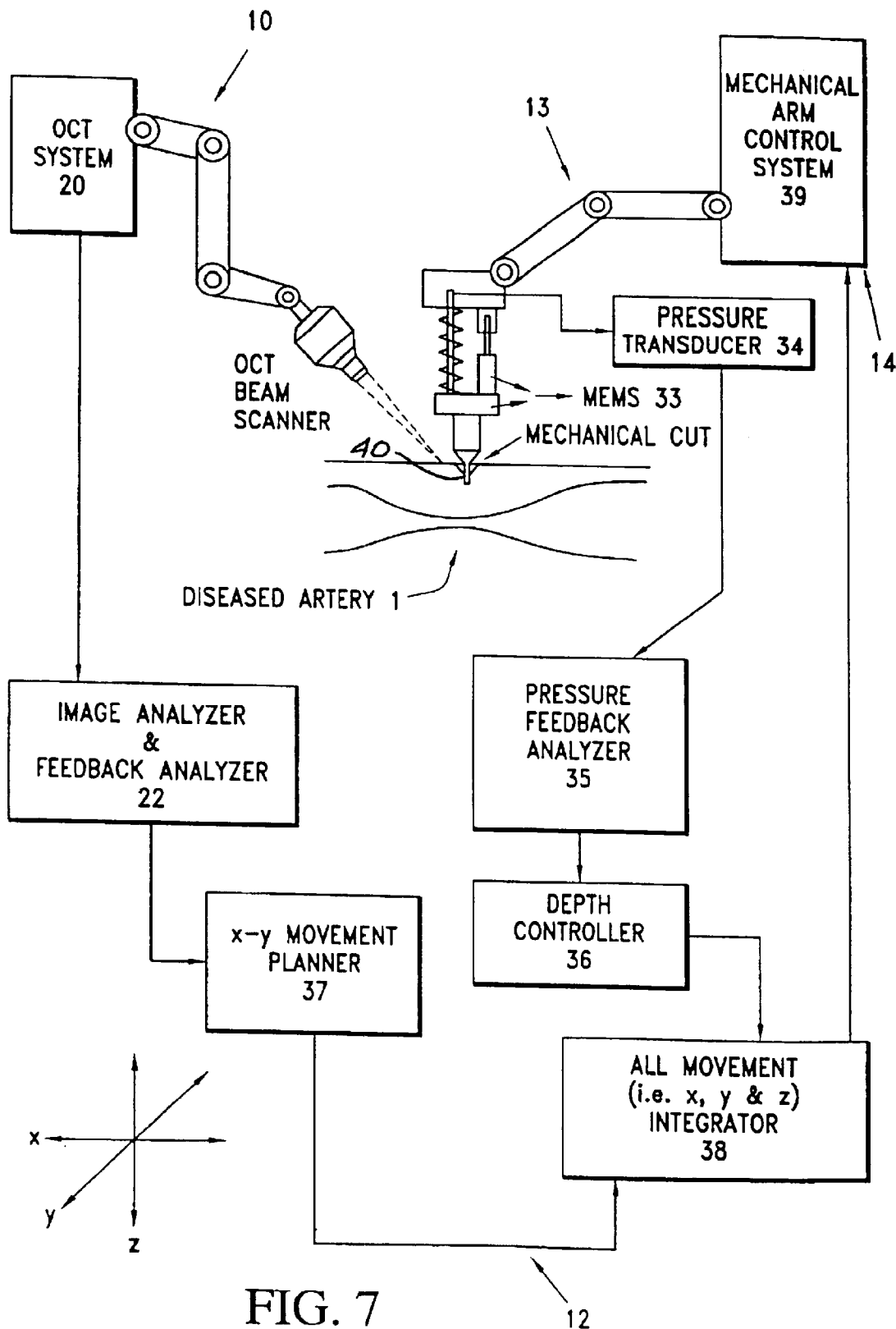
FIG. 7 is a schematic view of the apparatus of FIG. 5 in accordance with a second preferred embodiment of the invention.

FIG. 7 illustrates an apparatus of a second preferred embodiment of the invention, in use. In this embodiment, the ablating apparatus 13 is a mechanical ablation apparatus comprising single or multiple sharp microtome blades 40 mounted on piezo-electric pressure transducers 34, for feedback control of pressure applied and therefore depth incised (along the z-axis, as described below). The pressure transducer(s) 34 are in turn mounted on a MEMS (micro-electro-mechanical system) 33 to control the length and direction of incision (along the x and y axes). The ablating controller 14, in response to signals from the survey controller 12, thus controls the movement of the blade(s) 40 in three dimensions (x, y and z directions) to perform appropriate ablation (cutting).

In particular, as shown in FIG. 7, a pressure feedback analyser 35 is responsive to the pressure transducers 34 and provides data to a depth controller 36. The OCT system 20 and image analyser and feedback analyser 22 (which correspond to the same parts of the embodiment of FIG. 6) provide data to an x-y movement planner 37. The data from the x-y movement planner 37 and the depth controller 36 are provided to a movement integrator 38 which controls a mechanical arm control system 39 of the ablating apparatus 14. The movement of the blade(s) 40 is thereby accurately controlled in three dimensions.

Typically a few longitudinal and transverse partial thickness incisions are enough for achieving the objective of reducing effective arterial wall thickness. Increased flexibility due to reduced effective arterial wall thickness allows distension of the blood vessel under physiological blood pressure. This leads to increased blood flow through the artery, which was previously stenosed.

As the skilled person will appreciate, other types of ablation apparatus may be used according to the ablation technique employed. Such techniques include electromagnetic, photonic and ultrasound ablation.

Numerous variations may be made to the described embodiments. It is intended to include all such variations and modifications which fall within the spirit and scope of the present invention.

What is claimed is:

1. An apparatus for relieving arterial blockage by increasing flexibility of an arterial wall without entering into a lumen of an artery, the apparatus comprising:
   i) surveying means for surveying a thickness of an aarterial wall;
   ii) external ablating means for ablating an exterior of the arterial wall to increase the flexibility of the arterial wall; and
   iii) an ablating controller means for controlling the external ablation of the arterial wall by the external ablating means, said ablating controller means being interfaced between said surveying means and said external ablating means and being responsive to a signal from said surveying means, the signal relating to the arterial wall thickness.

2. The apparatus as claimed in claim 1, wherein said surveying means includes means to produce a 3D image of the arterial wall.

3. The apparatus as claimed in claim 2, wherein said surveying means is selected from a group of surveying means consisting of: mechanical imaging, ultrasound, magnetic resonance imaging, computed tomographic imaging using electromagnetic radiation and photonic imaging.

4. The apparatus as claimed in claim 1, wherein said ablating means includes a laser.

5. The apparatus as claimed in claim 4, wherein the laser is a femo-second pulsed laser.

6. The apparatus as claimed in claim 5, wherein the pulsed laser includes means for producing pulses which are of 20 to 100 fs duration.

7. The apparatus as claimed in claim 5, wherein the pulsed laser produces radiation of 3–5 $J/cm^2$ fluence.

8. The apparatus as claimed in claim 4, wherein the pulsed laser produces a laser spot diameter between 10 to 100 $\mu m$.

9. The apparatus as claimed in claim 2, wherein the ablating controller means includes means to control ablation to provide a uniform residual arterial wall.

10. The apparatus as claimed in claim 2, wherein the ablating controller means includes means to controls ablation to provide a plurality of blind holes in the exterior of the arterial wall.

11. The apparatus as claimed in claim 2, wherein the ablating controller means includes means to control ablation to provide a plurality of furrows in the exterior of the arterial wall.

12. The apparatus as claimed in claim 1 wherein said ablating means includes a mechanical ablation device including at least one blade mounted on at least one pressure sensing transducer.

13. The apparatus of claim 12 wherein said at least one pressure sensing transducer is mounted on a micro-electro-mechanical controller for controlling an incision of said at least one blade along two axes.

* * * * *